United States Patent [19]

Trowbridge et al.

[11] Patent Number: 5,667,781

[45] Date of Patent: Sep. 16, 1997

[54] ENHANCED INHIBITION OF TUMOR CELL PROLIFERATION USING A COMBINATION OF TWO MONOCLONAL ANTIBODIES TO THE HUMAN TRANSFERRIN RECEPTOR

[75] Inventors: Ian S. Trowbridge, San Diego, Calif.; Raymond Taetle, Tucson, Ariz.; Suhaila N. White, Poway, Calif.

[73] Assignees: The Salk Institute for Biological Studies, San Diego; The Regents of the University of California, Oakland, both of Calif.

[21] Appl. No.: 767,786

[22] Filed: Sep. 30, 1991

Related U.S. Application Data

[63] Continuation-in-part of Ser. No. 500,035, Mar. 27, 1990, abandoned.

[51] Int. Cl.$^6$ ................................................. A61K 39/395
[52] U.S. Cl. ..................................... 424/143.1; 435/70.21; 435/334; 435/343.2; 435/344; 530/388.22; 530/388.75; 530/388.8
[58] Field of Search ................................ 424/85.8, 143.1; 435/70, 21, 240.27; 530/388.22, 388.75, 388.8; 935/107, 108

[56] References Cited

U.S. PATENT DOCUMENTS 5,182,107  1/1993  Friden ........................... 424/85.91

OTHER PUBLICATIONS

White et al. (1990) Combinations of anti-transferrin receptor monoclonal antibodies . . . Cancer Research 50:6259–6301.
Trowbridge et al. (1982) Monoclonal antibody to transferrin receptor blocks transferrin . . . PNAS 79:1175–1179.
Sugita et al. (1986) Use of a cocktail of monoclonal antibodies and human complement . . . Int. J. Cancer 37:351–357.
Taetle et al. (1986) Mechanism of growth inhibition by anti-transferrin receptor monoclonal antibodies Cancer Res. 46:1759–1763.
Goding, J.W. (1983) Monoclonal Antibodies: Princples and Practice Acedemic Press, Inc., New York, pp. 56–91.
Trowbridge et al. (1987) Monoclonal Antibodies to Transferrin Receptor and Assay of Their Biological Effects, Meth. Enzymol. 147:265–279.
Trowbridge et al. (1984) Monoclonal Antibodies to Transferrin Receptors in: "Monoclonal Antibodies to Receptors . . . " M. F. Greaves, Ed. Chapman & Hall, London pp. 237–264.
Waldmann, T.A. (1991) Monoclonal Antibodies in Diagnosis & Therapy Science 252:1657–1662.
Trowbridge et al. (1981) Human cell surface glycoprotein related to cell proliferation . . . PNAS 78:3039–3043.
Sauvge et al (1987) Cancer Res. 47:747–753.
Gatter et al (1983) J. Clin. Pathol. 36:539–545.
Ceriani et al (1987) Cancer Res. 47:532–540.
Weis et al (eds) "Handbook of Experimental Immunology", vol. 4., Blackwell Scientific Publications Oxford, pp. 131.1–132.14.
Harris et al (1993) Trends in Biotech. 11:42–44.
Gregoriadis et al. (1993) Trends in Biotech. 11:440–442.
Thorpe (1993) Trends in Biotech. 11:40–42.
Fitzer–Schiller (1993) The Washington Post, Jan. 19, 1993, p. D3.
Waldmann, T.A. (1989) Cancer Survey 8(4):.
Grossbard et al. (1992) Blood 80(4):863–878.
Monks et al (1991) J. Nat'l Cancer Inst. 83:757–766.

*Primary Examiner*—Toni R. Scheiner
*Attorney, Agent, or Firm*—Fitch, Even, Tabin & Flannery

[57] ABSTRACT

Combinations of monoclonal antibodies which are highly effective for inhibiting cell growth and methods for inhibiting cell growth employing novel combinations of monoclonal antibodies are disclosed. The antibodies employed are capable of binding to the human transferrin receptor glycoprotein and, in combination, usually exhibit a substantially greater inhibition of cell growth than either of the antibodies individually when administered in comparable amounts, e.g. at saturation conditions. In preferred combinations, at least one member of the combination is individually highly effective to inhibit cell growth and at least one other member of the combination is individually substantially ineffective to inhibit cell growth. Combinations are selected based upon an in vitro screening test using CCRF-CEM cells which express the human Tf receptor.

24 Claims, 4 Drawing Sheets

ENHANCED INHIBITION OF TUMOR CELL PROLIFERATION USING A COMBINATION OF TWO MONOCLONAL ANTIBODIES TO THE HUMAN TRANSFERRIN RECEPTOR

This application is a continuation-in-part of our U.S. application Ser. No. 07/500,035 filed on Mar. 27, 1990, now abandoned.

This invention was made with Government support under Grant No. U01 CA-37641 awarded by the National Cancer Institute of the National Institutes of Health. The Government has certain rights in the invention.

The present invention is related to monoclonal antibodies. In one aspect, the present invention is related to combinations of monoclonal antibodies. In another aspect, the present invention is related to novel applications of combinations of monoclonal antibodies for use in the inhibition of cell growth.

BACKGROUND OF THE INVENTION

Antibodies have long been used in medical diagnosis, e.g., determining blood types, and in biological experimentation. The usefulness of antibodies, however has been somewhat limited, as their complexity and diversity have made it very difficult to obtain homogeneous antibodies. Antibodies are complex protein or protein-based molecules which are produced by the immune systems of animals to protect the animal against foreign substances. Antibodies for medical use are generally obtained by injecting an animal with a foreign substance which will stimulate the animal's immune system and, most commonly, isolating an antibody fraction from the peripheral blood serum or from the ascitic fluid. The antibody fraction contains antibodies specific to the injected foreign substance as well as various other antibodies produced by the animal. By known techniques, it may be possible to substantially isolate an antibody specific to the particular foreign substance. However, even when an antibody for a particular foreign substance is isolated, such antibody is actually a mixture of several antibodies which recognize various antigenic determinants of the foreign substance or related substances. While some individual antibody molecules may be highly specific, recognizing only a certain foreign substance or portion thereof, other antibody molecules may be less selective, recognizing not only the subject foreign substance, but other substances as well. Because it is generally practically impossible to separate all related antibodies, even the most carefully purified antibody fractions may react with more than one substance.

In recent years, techniques of producing monoclonal antibodies (MAbs) have been developed which make it possible to obtain homogeneous, highly specific antibodies. Generally, such antibodies are produced by immunizing an animal with a protein fraction or other foreign substance, obtaining antibody-producing cells from the animal, and fusing the antibody-producing cells with strains of myeloma cells, e.g., tumor cells, to produce hybridomas which are isolated and cultured as monoclones. The monoclonal hybridomas may either be cultured in vitro or may be grown as tumors in a host animal. Because each antibody-producing cell produces a single unique antibody, the monoclonal cultures of hybridomas each produce homogeneous antibodies which may be obtained either from the culture medium of hybridoma cultures grown in vitro or from the cells, ascitic fluid, or serum of a tumor-bearing host animal.

Not all of the hybridoma clones which result from fusing neoplastic cells with antibody-producing cells are specific for the desired foreign substance or antigen (the substance with which the antibody reacts). This is because many of the hybridomas will make antibodies which the animal has produced to react with other foreign substances. Even antibodies against the subject antigen will differ from clone to clone because antibodies produced by different cells may react with different antigenic determinants of the same molecule. From each clone, therefore, it is necessary to obtain the resulting antibody or the antibody-containing medium, serum or ascitic fluid and test both its reactivity with the subject antigen and its specificity by determining what other substances, if any, it recognizes. While the necessity of characterizing the antibody of each clone adds to the complexity of producing monoclonal antibodies, the wide variety of homogeneous antibodies which may be obtained gives investigators a number of very precise tools to map the structure and development of somatic cells.

The availability of homogeneous, highly specific MAbs dramatically increases the value of antibodies as a diagnostic, experimental and therapeutic tool. Use of MAbs for tumor and virus detection has been described in U.S. Pat. Nos. 4,172,124 and 4,196,265.

MAbs are particularly suitable for studying the pathways and processes by which cells differentiate into different types of somatic cells to produce the various tissues of the body. Cell differentiation is a complex subject, and understanding of the processes involved is only beginning. Proteins which are specific to particular cell types and which may be detected by different MAbs, serve as precise markers for the study of cell development and differentiation. MAbs which are specific for given proteins not only may be used to ascertain the presence of known proteins in a cell, they may also be used to detect substances heretofore undiscovered. Theoretically it may be possible to eventually obtain MAbs for every macromolecule in the body to permit the complete mapping of the various proteins, etc.

An important topic in the field of cell differentiation is the study of cells which, in their mature form, are non-proliferating, being derived from actively proliferating stem cells. Many examples of such cells may be found in the peripheral blood. Red blood cells and leukocytes arise from stem cells in the bone marrow, and both are normally non-proliferating as mature cells in the blood stream. Misdevelopment of somatic cells may lead to cancers, including blood cell-related cancers such as myelomas and leukemias, and MAbs are useful for determining the proteins present in such cells to more fully trace their development and derivation.

In recent years, MAbs have been developed which react with the human transferrin (Tf) receptor. At least one of such MAbs blocks Tf binding to cells and thereby interferes with the ability of cells to proliferate. See, for example, U.S. Pat. No. 4,434,156, the disclosure of which is hereby incorporated by reference in its entirety. These MAbs are shown to be useful for inhibiting cell growth.

In Sauvage et al., *Cancer Research*, 47:747–753 (1987), two rat MAbs which bind to the murine Tf receptor are described which both block Tf receptor function and inhibit the growth of SL-2 leukemic cells in vitro when administered individually. In addition, the Sauvage article reports that one of these single anti-Tf MAbs, i.e., R17 208, in combination with an anti-Thy-1 MAb, which is directed to the Thy-1 glycoprotein and not to the murine Tf receptor, shows greater inhibitory effect against SL-2 leukemic cell growth in vitro. It then speculates that, based upon a test of only these two antibodies, it may be useful to use an anti-Tf antibody with one that activates a host immunological effector mechanism.

Despite the advances represented by these developments, there is always room for advancements which provide even more effective means for the regulation of cell growth.

SUMMARY OF THE INVENTION

It has now been discovered that certain combinations of MAbs are substantially more effective for inhibiting the growth of proliferating cells than would be expected from a consideration of only the activities of the individual MAbs. The combinations of the present invention are useful, for example, for killing or inhibiting the growth of certain human cells, in particular tumor cells, and most particularly Tf-receptor-positive tumor cells.

As is the case with MAbs against most other potential cell surface target antigens, a major factor limiting previous studies of the efficacy of anti-Tf receptor MAbs as antitumor agents has been the inability to generate large numbers of MAbs in order to identify those with optimal properties. The availability of purified recombinant human Tf receptor, produced, for example, in a baculovirus expression system [*J. Biol. Chem.* 263:13386–13392. (1988)] in sufficient quantity for immunization and hybridoma screening, has allowed this problem to be overcome and has further enabled generation of many new MAbs against the external domain of the human Tf receptor. In accordance with the present invention, it has surprisingly been found that certain pairs of anti-Tf receptor MAbs inhibit the in vitro growth of a panel of human hematopoietic cells more effectively than either of the two MAbs separately, and on the basis of straightforward in vitro testing of MAbs using the standard CCRF-CEM leukemic cell line, it can be simply determined which particular pairs of MAbs will exhibit anti-tumor activity in vivo with respect to human transferrin receptor positive cells. Such combinations of MAbs, in contrast to the individual MAbs administered separately, have been demonstrated to markedly inhibit the growth of established subcutaneous tumors of CCRF-CEM leukemia cells in nude mice and induce tumor regressions.

DETAILED DESCRIPTION OF THE INVENTION

In accordance with the present invention, there is provided a method of inhibiting tumor cell growth in a mammal, which method comprises administering to said mammal an effective dose of a combination containing at least a first and a second MAb, wherein each of said antibodies is capable of binding to the human transferrin receptor glycoprotein, and wherein said combination of at least two antibodies is more effective to inhibit such cell growth than when said antibodies are administered individually.

In a presently preferred aspect of this embodiment of the present invention, two antibodies are administered, at least one of which antibodies is not effective to block the binding of Tf to said receptor glycoprotein; however, both antibodies may fall within this category. It may be particularly preferred that one of said antibodies, individually, has substantially no inhibiting effect upon tumor cell growth and that the second antibody individually blocks the binding of Tf to the receptor glycoprotein. It is especially preferred that both of the antibodies of the pair are capable of simultaneously binding to the receptor glycoprotein.

In accordance with another embodiment of the present invention, there is provided a therapeutic composition for inhibiting tumor cell growth in a mammal, which composition comprises an effective amount of a combination of at least a first MAb and a second MAb and a pharmaceutically acceptable carrier, wherein each of said antibodies is capable of binding to the human transferrin receptor glycoprotein, and wherein said combination of antibodies is more effective to inhibit growth of certain mammalian tumor cells than are either of said antibodies when administered individually. In a preferred aspect of this embodiment of the present invention, at least one of said antibodies is not effective to block the binding of Tf to said receptor glycoprotein. It may be particularly preferred that second antibody individually blocks the binding of Tf to the receptor glycoprotein; however, that antibody can also individually have substantially no inhibiting effect upon tumor cell growth. It is especially preferred that both of the antibodies of the pair are specific to different epitopes of the human Tf receptor glycoprotein and are capable of simultaneously binding to the receptor glycoprotein.

In accordance with yet another embodiment the present invention, there are provided novel IgG-class MAbs referred to hereinafter by the designations D65.30 (ATCC Accession No. HB-10394, deposited Mar. 27, 1990), A27.15 (ATCC Accession No. HB-10395, deposited 3/27/90), E2.3 (ATCC Accession No. CRL-10746, deposited May 5, 1991), 341.2, 232.3, and other similar antibodies. The cell lines with corresponding ATCC deposit numbers are deposited at the American Tissue Culture Collection, 12301 Parklawn Drive, Rockville, Md. 20852.

MAbs employed in the practice of the present invention are specific for the external domain of the human Tf receptor (which is found on the surface of dividing cells, particularly proliferating tumor cells). The Tf receptor glycoprotein has been characterized as having a monomer molecular weight of about 95,000, as determined by its migration on SDS polyacrylamide gel under reducing conditions, and existing in its native state as a disulphide bonded dimer. Omary et al., (1980) *Nature*, 286, 888–891; Judd et al., (1980) *J. Exp. Med.*, 152, 1430–1435; Trowbridge and Omary (1981) *Proc. Nat. Acad. Sci. U.S.A.* 78, 3039–3043; Sutherland et al., (1981) *Proc. Nat. Acad. Sci. U.S.A.* 78, 4515–4519.

Purified human Tf receptor glycoprotein can be obtained from natural sources, recombinantly produced material, or the like, and introduced into animals to induce the production of antibodies to the glycoprotein, which is found on the surface of the hematopoietic cells. Any immunogen containing part of all of the external domain of the human Tf receptor glycoprotein or crossreactive material, including intact human cells and synthetic peptides, may also be used instead of purified receptor although the latter is preferred. The animal chosen for inoculation is not critical, but it is preferred to use strains which are well characterized, e.g., strains of murines such as rats, mice, and the like. Furthermore, various murine-derived neoplastic cells are also available as well-characterized cultures. Hence, mice are chosen for production of the antibodies hereindescribed, although it is to be understood that the invention is not limited to the use of murine-developed antibodies, nor to MAbs produced in hybridoma cells.

Methods of producing MAbs of this general type by recombinant DNA methods in bacteria, plants and other animal cells are known to those skilled in the art. Further, murine MAbs derived from hybridomas may be advantageously modified by recombinant DNA techniques to produce antibody fragments or to humanize murine MAbs.

BALB/c mice are inoculated subcutaneously with 50 µg of recombinant human transferrin receptor, as produced in a baculovirus expression system, mixed with complete Freunds adjuvant. After 6 weeks, the mice are inoculated with a booster of at least 50 µg of the purified fraction of the external domain of the receptor, given intravenously in saline. Four days after the second inoculation, the mice are sacrificed and their spleens are taken. A spleen cell suspension is prepared, and the resulting cell suspension is washed by two centrifugations (800×g) in protein-free Dulbecco's modified Eagles medium.

Since the antibody-producing cells obtained from the spleen do not independently reproduce, and thus cannot be cultured, they are fused with cells which may be independently cultured either in vivo or in vitro. This is done so that the genetic and metabolic processes of the fused hybridomas have characteristics of each of the parent cells. It is intended that certain of the cells obtained will have the capability to independently reproduce and to produce the antibody of the antibody-producing parent cell. Some tumor cells, particularly myeloma cells, may be advantageously fused with antibody-producing cells to yield hybridomas. Although it is not necessary, it is preferred that the tumor cells and antibody-producing cells be derived from the same species to enhance the likelihood that the genetic and biochemical properties of the parent cells will be compatible and thus produce viable hybridomas. A number of myeloma cultures have been characterized, and herein, mouse-derived non-antibody-producing myeloma cell line SP2/0-Ag14 (Isacke, et al., *Immunogenetics* 23, 326–332 (1986)) is used to produce the hybridomas. It is to be understood that other tumor lines, which include but are not limited to P3, Y3, S194/5.XXO.BU.1, MPC-11 and their derivatives, may also be used. It is advantageous to select a myeloma line which does not produce antibodies so that the resulting hybrid will only produce antibody chains of the parent spleen or lymph node cell. This is particularly important when the antibody is used for therapeutic purposes, e.g., to regulate cell growth, where it is undesirable to introduce extraneous antibodies which could produce side reactions.

The myeloma cells are maintained in Dulbecco's modified Eagles' medium supplemented with 10% horse serum. $10^7$ myeloma cells and $10^8$ cells obtained from the mice immunized with recombinant human transferrin receptor are resuspended for fusion in a 45% solution (v/v) of polyethylene glycol 1500 according to the methods of Trowbridge (1978) supra. Cell hybrids are selected in hypoxanthine aminopterin thymidine (HAT) medium, all growth in HAT medium being indicative of successful hybridization of mouse spleen and mouse myeloma cells. The production of antibodies against the purified Tf receptor used to inoculate the mice was isolated, and tested by the ELISA assay described below in example 1. Hybrid cells are cloned by the method of limiting dilution in Falcon microtiter plates.

Clones of hybridomas may be grown in vitro according to known tissue culture techniques such as is described by Cotton et al, *Eur. J. Immunol.* 3, 136 (1973). Alternatively, hybridomas may be grown in vivo as tumors in a histocompatible animal or in athymic nude mice. The antibodies may be recovered from the in vitro culture medium or from the serum or ascitic fluid of the animal by means known in the art, e.g., Gerhard et al., *Proc. Natl. Acad. Sci.* 75, 1510–1514 (1978). In some cases it may be advantageous to obtain the antibodies directly from the cells of the culture or tumor.

Antibody from each clone was then screened for anti-Tf receptor MAbs by ELISA assay. Hybridomas that produced anti-Tf receptor antibodies were then cloned by limiting dilution and re-assayed by ELISA. ELISA assays can be carried out employing techniques well known by those of skill in the art, and described in greater detain herein in Example 1.

Anti-Tf receptor MAbs were then screened to determine which MAbs responded to the external domain of the human Tf receptor were identified by the ability to bind to viable CCRF-CEM cells, as determined by FACS analysis. The CCRF-CEM cell line is a human T-cell leukemia line CEM which was grown at the Children's Cancer Research Foundation in Boston, Mass., and which is on deposit with the ATCC under Accession No. CCL-119.

When a useful hybridoma clone is produced it is generally advantageous to reclone the cell line to avoid overgrowth of cultures with variant cells no longer producing antibody. The reclones produce MAbs which hybridize to the same epitope of the glycoprotein as the parent. Since the hybridoma contains some, but not all, of the genetic material of each parent cell, the full characteristics of the hybridoma are not known. Often a hybridoma clone, due to original genetic deficiency or subsequent chromosome loss, after several passages may lose its ability to reproduce and/or to produce the particular antibody. Accordingly, it is important, soon after the initial hybridization, that a hybridoma clone of interest is recloned to insure the availability of functioning strains of the antibody-producing hybridoma. Cell line cultures identified as D65.30, A27.15, B49.1, B77.2, C45.1, D11.1, 148.1, 232.3, 289.2, 342.2, 417.1, W48.5, HS.10, H88.1, H56.42, 128.1, 144.1, 235.1, W59.2, Z35.2, A11.1, A17.3, B27, C95.7, D79.20, D86.13, E2.3, 341.2, 398.1, 454.1, 456.1 and W51.1, as well as derivatives thereof, produce MAbs specific for the Tf receptor glycoprotein. The D65.30 and A27.15 cell lines are deposited at the American Tissue Culture Collection, 12301 Parklawn Drive, Rockville, Md. 20852 as indicated above, and produce MAbs that are examples of those useful in the present invention.

MAbs contemplated for use in the combinations of the present invention fall generally into three classes. The first class includes antibodies which bind to the Tf receptor but, when administered alone to CCRF-CEM cells, provide little if any inhibition of growth of said CCRF-CEM cells, and on this basis they are referred to herein as being ineffective to block cell proliferation. A number of exemplary antibodies which satisfy the above criteria have been produced using the techniques discussed hereinbefore and are referred to by the following code designations: B3/25, B49.1, B77.2, C45.1, D11.1, 342.2, 417.1, W48.5, H8.10, H88.1, H56.42, 128.1, 144.1, 235.1, W59.2, Z35.2, A11.1, A17.3, B27, C95.7, D79.20, D86.13, E2.3, 398.1, 454.1, 456.1, and W51.1. MAb B3/25 was deposited at ATCC under Accession No. CRL-8034 on Sep. 19, 1980.

Additional antibodies contemplated for use in the practice of the present invention include a second class of antibodies which, when administered alone, inhibit, at least to a substantial degree, the growth of CCRF-CEM cells, as well as other human cell lines which possess human Tf receptors, such as KG-1, HL-60 or the like. Exemplary antibodies which satisfy the criteria of binding to Tf receptor and inhibiting cell growth include: 42/6 (ATCC Accession No. HB-8094, deposited Oct. 9, 1981), D65.30, A27.15, 232.3 and 341.2. A third class of antibodies is a subclass of the second class of antibodies which, when administered alone, both block at least to a substantial degree the ability of Tf to bind to the Tf receptor, and inhibit at least to a substantial degree the growth of CCRF-CEM cells (as well as other human cell lines as described hereinabove). MAb 42/6 is an example.

Combinations of such antibodies are easily selected based upon the results of straightforward in vitro screenings carried out using a standard cell line, e.g. the CCRF-CEM leukemic cell line (as described hereinafter) or the HL-60 cell line or the like. Pairs of MAbs are chosen which inhibit the growth of such cells to a substantially greater extent than do either of the MAbs individually when administered in saturation concentrations. The amount of greater effectiveness is necessarily relative, and if one antibody is particularly effective individually, e.g. D65.30, the difference exhibited by the combination will not be as great as when neither antibody is particularly individually effective. The two antibodies desirably bind to different epitopes of the human Tf glycoprotein receptor so they should bind simultaneously. Although one of them preferably does not individually block transferrin binding, the other may, but need not, block Tf binding.

The ratio of antibodies employed in the practice of the present invention can vary widely and still produce combinations that are more effective to inhibit cell growth than either of the individual antibodies. Typically, the ratio of first antibody (the antibody which is not effective to substantially inhibit cell growth) to the second antibody will fall in the range of about 0.5:1 up to 5:1. Preferably the ratio of first antibody to second antibody will fall in the range of about 1:1 up to 2:1.

When employed for therapeutic purposes, the inventive combination of antibodies can be administered in a wide variety of ways, as those of skill in the art are well aware. A combination of at least two antibodies and a pharmaceutically acceptable carrier are usually administered to a subject, e.g. a human. A third MAb specific to a different epitope or antigenic-site may also be included.

A wide variety of pharmaceutically acceptable carriers can be employed in the practice of the present invention, as can readily be determined by one of skill in the art. Presently preferred are liquid carriers, such as, for example, phosphate buffered saline or other isotonic, neutral aqueous solutions. The concentration of antibody combinations in said carrier can vary widely. The actual concentration of MAbs in carrier will vary as a function of the mode of administration, total target dosage is the individual being treated, handling and storage considerations, and so on.

Typical means of administration include iv and ip infusion or injection. The therapeutic combination is preferably administered at a daily dosage level of between about 0.1 and about 15 mg. per kilogram of body weight of the recipient; more particularly the combination of antibodies is administered so as to bring the antibody concentration in the serum of the recipient to a level of at least about 1 µg/ml. and preferably to a level of at least about 10 µg/ml.

The inventive method is particularly useful for the treatment of a variety of abnormal cell growth states, e.g., leukemia cell growth, melanoma cell growth, hematopoietic tumor cell growth, erythroleukemic tumor cell growth, and the like. In general, the inventive method is useful for inhibiting cell growth of normally or abnormally dividing cells, particularly hematopoietic cells, and leading to the death of the cells. The invention is considered to be particularly effective in combatting the growth of cells which express the human Tf-receptor and which are referred to herein as human Tf-receptor-positive cells. As demonstrated in the Examples which follow, the inventive combination of MAbs is cytotoxic, i.e., cause the death of many treated cells, as opposed to being cytostatic, i.e., merely arresting the growth of treated cells.

The invention will now be described in greater detail with reference to the following non-limiting examples.

EXAMPLE 1

Preparation of MAbs. Recombinant human Tf receptor was produced in a baculovirus expression system as described by Domingo and Trowbridge [*J. Biol. Chem.* 263:13386–13392 (1988)] and purified on a human Tf affinity column, essentially as previously described by Anderson, G. J., Mackerras, A., Powell, L. W., and Halliday, J. W. [*Biochim. et Biophys. Acta* 884:225–233 (1986)] except that 1M NaI was included in the final elution buffer instead of 1M KCl. The yield of recombinant human Tf receptor was ~0.5 mg/l of cells. BALB/c mice were immunized with 50 µg of purified receptor glycoprotein in complete Freund's adjuvant at a subcutaneous site on the back. Following a similar immunization two weeks later, mice were immunized at various times later with an intravenous injection of 50 µg of recombinant Tf receptor in the saline. Three days later, the spleens of the immunized mice were removed and fused with SP2/0-Ag14 myeloma cells essentially as described by Isacke, C. M., Sauvage, C. A., Hyman, R., Lesley, J., Schulte, R., and Trowbridge, I. S. [*Immunogenetics* 23:326–332 (1986)]. Cells from the fusion of 1×10⁸ spleen cells and 1×10⁷ myeloma cells were plated out into five 96-well microtiter plates (Costar, Cambridge, Mass., #3596) and hybridoma supernatants were then screened for anti-Tf receptor MAbs by ELISA assay 10 to 21 days later. Hybridomas that produced anti-Tf receptor antibodies were then immediately cloned by limiting dilution and reassayed by ELISA. MAb-containing ascitic fluid was obtained by intraperitoneal injection of $5 \times 10^6$ cloned hybridoma cells into BALB/c mice previously primed with 0.4 ml pristane (Aldrich Chemical Co., Milwaukee, Wis.) 1–3 weeks earlier. MAbs were then partially purified from the ascitic fluid by a 50% ammonium sulfate precipitation.

Isotyping of the MAbs was performed using an ELISA isotyping kit according to the manufacturer's instructions (Zymed Laboratories Inc., San Francisco, Calif., Mono Ab—ID EIA Kit). The ELISA assay for preliminary screening of the hybridoma supernatants was performed by coating 96-well immunoplates (Nunc Inc., Naperville, Ill., Maxisorp F96) with 50 ng per well of purified recombinant human Tf receptor in 50 mM Na bicarbonate buffer (pH9.6) overnight at 4° C. The ELISA assay was then performed essentially as previously described by Voller, A., Bidwell, D. E., and Bartlett, A. in "Enzyme immunoassays in diagnostic medicine." *Bulletin of the World Health Organization* 53:55–56 (1976). MAbs against the external domain of the human Tf receptor were then identified by their ability to bind to viable CCRF-CEM cells as determined by FACS analysis on a Los Alamos design flow cytometer [as described by Lesley, J., Hyman, R., Schulte, R., and Trotter, J. in *Cell. Immunol.* 83:14–25 (1984)] Cells ($2 \times 10^6$) were stained with 100 ml of hybridoma supernatant followed by saturating amounts of goat anti-mouse Ig (Organon Teknika-Cappel, Westchester, Pa.) as the second stage antibody.

MAbs 42/6 and B3/25 against the human Tf receptor have been previously described by Trowbridge, I. S., and Lopez, F. [*Proc. Natl. Acad. Sci. USA* 79:1175–1179 (1982)]; and by Trowbridge, I. S., and Omary, M. B. [*Proc. Natl. Acad. Sci. USA* 78:3039–3043 (1981)].

EXAMPLE 2

Culture and Assays Employed

Cell Lines and Tissue Culture. The human tumor cell lines used in these studies CCRF-CEM, HL-60, KG-1 (granulocytic leukemic), K562 (human erythroleukemic), Namalwa, U937, and M21 (melanoma) have been described previously by Taetle, R., Honeysett, J. M., Trowbridge, I. S. [*Int. J. Cancer* 32:343–743.7 (1985)]; they were routinely subcultured in RPMI 1640 medium supplemented with either 5% fetal bovine serum or 8% defined calf serum. The CCRF-CEM sub-line grows as a subcutaneous tumor in nude mice.

HL-60 Colony-Forming Inhibition Assay. The cytotoxic activity of anti-Tf receptor MAbs was assessed in HL-60 colony-forming assays as previously described Taetle, R., Honeysett, J. M., and Bergeron, R. in *J. Natl. Cancer Inst.* 81:1229–1235 (1989). Briefly, log phase cells were washed and cultured with RPMI 1640 medium and 10% fetal bovine serum, alone or with 10 mg/ml anti-Tf receptor MAbs either singly or in combination. After 1–5 days, cells were washed and equal numbers of total cells plated in a colony-forming assay. Aggregates of greater than 50 cells were scored as colonies after 10 to 14 days of incubation. Control cultures in these studies grew 764±17 colonies per $10^4$ cells.

Figure 1:
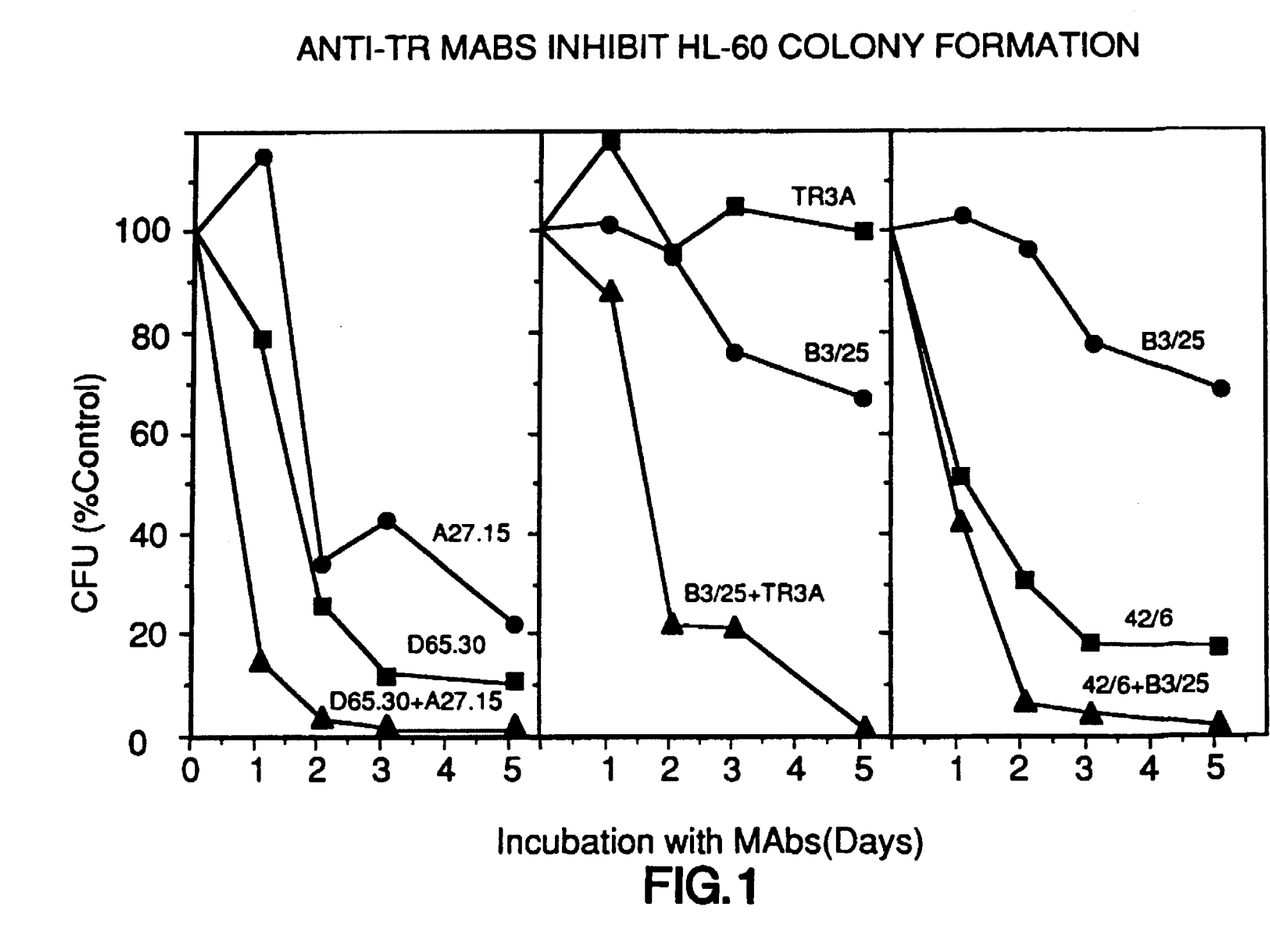
FIG. 1 shows graphs which illustrate inhibition of HL-60 colony formation by combinations of anti-human Tf receptors MAbs. HL-60 cells were grown in the presence of anti-Tf receptor MAbs at concentrations of 10 µg/ml for the number of days indicated. The cells were then washed and colony-forming assays were performed as described in Example 2. Results are the mean of duplicate experiments, with CFU=colony-forming unit.

The results of the colony-forming inhibition assay are shown in FIG. 1. After 2 days, colony formation by cells treated with the combination of MAbs D65.30 and A27.15 was inhibited by greater than 90%, whereas, colony formation by each MAb individually was 75% and 65%, respectively. After 5 days, inhibition of colony formation by cells treated with the same combination was greater than 95%, whereas, inhibition of colony formation by each MAb individually was approximately 90% and 80%, respectively.

Similarly, the MAb combinations B3/25 with TR3A and 42/6 with B3/25 inhibited colony formation to a greater degree when administered in combination versus when administered individually.

Cell Cycle Analysis. DNA content of cells cultured with or without anti-Tf receptor MAbs was determined using propidium iodide staining as previously described Taetle, R., Honeysett, J. M., and Bergeron, R. Supra.

$^{59}$Fe Uptake Experiments. Human Tf was labelled with $^{59}$Fe by the method of Bates and Schlabach [*J. Biol. Chem.* 248:3228–3232 (1973)]. For $^{59}$Fe uptake experiments, log phase HL-60 cells were washed twice in serum-free RPMI 1640 medium, and then cultured for 24 hours in serum-free RPMI medium containing ethanolamine, insulin and selenium in the presence of 4 µg/ml $^{59}$Fe-labelled Tf with or without anti-Tf receptor MAbs at a concentration of 50 µg/ml. [Taetle, R., Rhyner, K., Castagnola, J., To, D., Mendelsohn, J. *J. Clin. Invest.* 75:1061–1067 (1985)] After various periods of time, cells were washed three times with RPMI 1640 medium and cell-associated $^{59}$Fe determined by counting in a gamma counter.

In Vivo Anti-Tumor Assay. The anti-tumor activity of anti-Tf receptor monoclonal antibodies was determined using CCRF-CEM cells grown as a subcutaneous tumor in nude mice. 4–6 week old female (Nu/Nu) nude mice were obtained from Charles Rivers Laboratories (Wilmington, Mass.) and inoculated with $2 \times 10^7$ CCRF-CEM cells at a subcutaneous site on the back. Animals were then given intraperitoneal injections of MAbs at various times, and tumor size was determined by two perpendicular measurements of tumor diameters using calipers. Tumor size was then calculated according to the formula: tumor size=(width, mm)$^2 \times$(length, mm)/2, as previously described by Taetle, R., Rosen, F., Abramson, I., Venditti, J., and Howell, S. [*Cancer Treatment Reports* 71:297–304 (1987)].

EXAMPLE 3

Evidence for Synergistic Effects with Combinations of Antibodies. 32 cloned hybridoma cell lines producing MAbs against the external domain of the human Tf receptor from fusions of spleen cells of BALB/c mice immunized with purified recombinant human Tf receptor were prepared as described above and are listed in Table 1. These were identified initially by their reactivity with the purified recombinant Tf receptor in an ELISA assay. They were then shown to recognize the external domain of the naturally-occurring human Tf receptor by their ability to bind to viable CCRF-CEM cells detected by FACS analysis. As shown in Table 1, the MAbs obtained were predominantly of the IgG$_1$ subclass (30 of 32 MAbs). MAbs were then tested individually for their ability to inhibit growth of the human T leukemic cell line, CCRF-CEM, in tissue culture.

CCRF-CEM cells were plated at a density of $2 \times 10^4$ cells per well in 1.0 ml of RPMI 1640 medium supplemented with 8% defined calf serum (Hyclone, Logan, UT) in 24-well tissue culture plates (#3524, Costar, Cambridge, Mass.). Antibodies, either singly or in combination, were added at a concentration of 50 µg/ml to duplicate wells, and on Day 4 and Day 7, cells from duplicate wells were harvested and counted twice using a Coulter counter. Replicate counts usually differed by <10%. Growth inhibition studies using K562, KG1, HL-60, and M21 cells were performed similarly. For dose dependence curves, assays were performed as above except the MAb concentrations used were varied.

The monoclonal antibodies used for these studies were partially purified from murine ascitic fluid by 50% (w/v)

ammonium sulphate precipitation and used at a concentration of 50 µg/ml; where combinations of antibodies were used, the total antibody concentration was maintained at about 50 µg/ml, typically with a ratio of antibodies of about 1:1.

The results presented in Table 1 are the average percent inhibition of cell growth on Day 7 in antibody-treated cultures compared to cell growth obtained with untreated control cultures:

$$\left(1 - \frac{\text{cells in MAb-treated cultures}}{\text{cells in untreated cultures}}\right) \times 100$$

TABLE 1

INHIBITION OF IN VITRO GROWTH OF CCRF-CEM CELLS BY ANTI-HUMAN Tf RECEPTOR MAbs ALONE OR IN COMBINATION

|  | | Antibody | % Inhibition of Growth[a] | | |
|---|---|---|---|---|---|
| | MAb[b] | Class | Alone | +D65.30 | +42/6 |
| | 42/6 | IgA | 62 | 66 | ND[c] |
| | D65.30 | IgG$_1$ | 65 | ND | 66 |
| Group A | A27.15 | IgG$_1$ | 40 | 93 | 92 |
| | B49.1 | IgG$_1$ | 0 | 91 | 88 |
| | B77.2 | IgG$_1$ | 0 | 92 | 87 |
| | C45.1 | IgG$_1$ | 15 | 92 | 89 |
| | D11.1 | IgG$_1$ | 13 | 91 | 91 |
| | 148.1 | IgG$_1$ | 33 | 94 | 91 |
| | 232.3 | IgG$_1$ | 38 | 95 | 91 |
| | 289.2 | IgG$_1$ | 30 | 94 | 92 |
| | 342.2 | IgG$_1$ | 27 | 93 | 91 |
| | 417.1 | IgG$_1$ | 17 | 94 | 91 |
| | W48.5 | IgG$_1$ | 0 | 94 | 91 |
| Group B | H8.10 | IgG$_1$ | 20 | 13 | 50 |
| | H88.1 | IgG$_1$ | 12 | 21 | 67 |
| | H56.42 | IgG$_{2b}$ | 17 | 14 | 39 |
| | 128.1 | IgG$_1$ | 0 | 4 | 69 |
| | 144.1 | IgG$_{2a}$ | 0 | 11 | 90 |
| | 235.1 | IgG$_1$ | 0 | 1 | 63 |
| | W59.2 | IgG$_1$ | 11 | 9 | 64 |
| | Z35.2 | IgG$_1$ | 13 | 16 | 62 |
| Group C | A11.1 | IgG$_1$ | 0 | 42 | 90 |
| | A17.3 | IgG$_1$ | 0 | 41 | 90 |
| | B27 | IgG$_1$ | 0 | 72 | 78 |
| | C95.7 | IgG$_1$ | 13 | 70 | 72 |
| | D79.20 | IgG$_1$ | 11 | 75 | 89 |
| | D86.13 | IgG$_1$ | 0 | 69 | 88 |
| | E2.3 | IgG$_1$ | 20 | 76 | 92 |
| | 341.2 | IgG$_1$ | 48 | 51 | 91 |
| | 398.1 | IgG$_1$ | 2 | 62 | 48 |
| | 454.1 | IgG$_1$ | 0 | 79 | 89 |
| | 456.1 | IgG$_1$ | 17 | 72 | 89 |
| | W51.1 | IgG$_1$ | 0 | 54 | 76 |

[a]CCRF-CEM cells were set up in duplicate cultures and cell counts made in duplicate on Day 4 and Day 7 of each culture using a Coulter counter. The results presented are the average percent inhibition of cell growth on Day 7 in antibody-treated cultures compared to untreated control cultures $$\left(1 - \frac{\text{cells in MAb-treated cultures}}{\text{cells in untreated cultures}}\right) \times 100$$

Replicate cell counts usually varied by less than 10%.
[b]MAbs were partially purified from murine ascitic fluid by 50% (w/v) (NH4)2SO4 precipitation and used at a concentration of 50 µg/ml.
[c]Not Determined Most of the antibodies tested, when administered individually, had little or no effect on the growth of CCRF-CEM cells (Table 1). However, one IgG, MAb D65.30, inhibited the growth of CCRF-CEM cells as effectively as the IgA MAb, 42/6, the only previously known anti-human Tf receptor MAb with substantial anti-proliferative activity, [Trowbridge, I. S., and Lopez, F. in Proc. Natl. Acad. Sci. USA 79:1175–1179 (1982)]. Several other IgG$_1$MAbs, most notably A27.15 and 341.2, also showed some inhibition of the growth of CCRF-CEM cells, but to a lesser degree.

The results that were obtained with individual monoclonal antibodies in combination with antibody No. D65.30 are striking and indicate that the various antibodies tested fall into three groups. Antibodies in Group A very markedly enhanced the growth inhibitory effects of MAb D65.30; whereas antibodies in Group B substantially decreased the growth inhibitory effects of MAb D65.30; while the remaining antibodies, grouped in Group C, had little or no effect on growth inhibition induced by MAb D65.30 alone. It is clear that certain of the MAbs (especially B49.1, B77.2 and W48.5), each of which alone has no effect on the growth of CCRF-CEM, act essentially synergistically with MAb D65.30 to inhibit proliferation, as both antibodies were present at saturation concentrations in the tests that were performed.

Similarly, many of the IgG MAbs tested in combination with antibody 42/6 gave greater inhibition of proliferation than did 42/6 alone, including antibodies that when tested singly did not have a detectable effect on the growth of CCRF-CEM cells.

The combination of MAbs D65.30 and 42/6, however, was not any more inhibitory than either of the single antibodies alone; and similarly, antibody 341.2, which itself exhibits significant inhibitory activity, does not increase the inhibition of growth induced by MAb D65.30.

Figure 2:
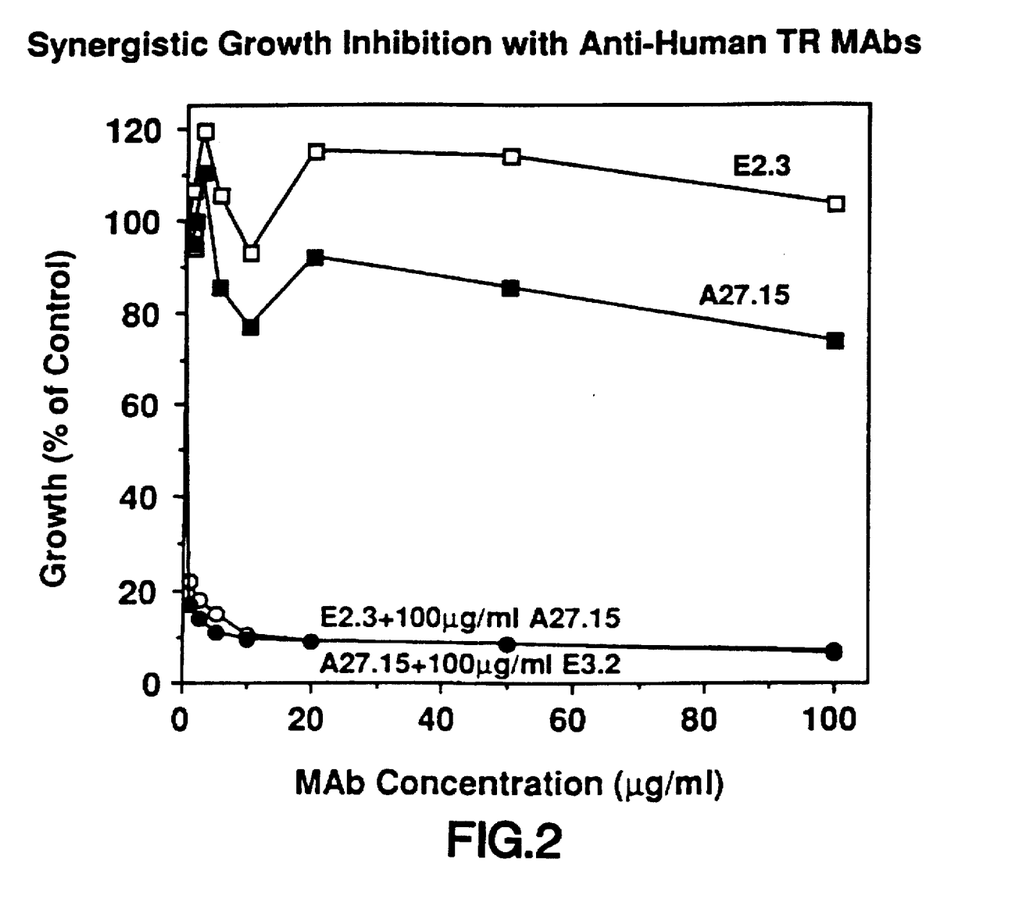
FIG. 2 shows dose-response curves which illustrate the antiproliferative effects of anti-Tf receptor MAbs E2.3 and A27.15 alone and in combination, with the concentration of the first MAb being as shown on the ordinate. CCRF-CEM cells were grown for 7 days in the presence of various concentrations of a single MAb or combinations of anti-Tf receptor MAbs as described in Example 3. Cell numbers in replicate cultures were determined by counting in a Coulter counter.

Another combination of MAbs, E2.3 (ATCC Accession No. CRL-10746) and A27.15, exhibits synergism over the administration of either antibody alone when tested in vitro. CCRF-CEM cells were grown for 7 days in the presence of 100 µg/ml of MAb E2.3 and 0–100 µg/ml of MAb A27.15. Similarly, CCRF-CEM cells were grown for 7 days in the presence of 100 µg/ml of MAb A27.15 and 0–100 µg/ml of MAb E2.3. The results are shown in FIG. 2. When the MAbs E2.3 and A27.15 were present in combination, they inhibited the growth of the CCRF-CEM cells by approximately 95% relative to cells which did not receive MAb treatment. When cells were grown in the presence of either MAb E2.3 and A27.15 alone, MAb E2.3 did not inhibit the growth of the CCRF-CEM cells, and A27.15 inhibited the growth by approximately 25%. Therefore MAbs E2.3 and A27.15 exhibit synergism over the administration of either antibody alone when tested in vitro.

The synergistic inhibitory effects of other combinations of anti-Tf receptor MAbs on the growth of CCRF-CEM cells have also been confirmed by dose response experiments using antibody B3/25 (ATCC accession number CRL-8034, deposited Sep. 19, 1980). The combination of B3/25 and 42/6 MAbs clearly inhibits the growth of CCRF-CEM cells more than the sum of the inhibition induced by either antibody alone, for all concentrations tested. Similarly, both B49.1 and B77.2 MAbs interact synergistically with MAb D65.30.

The combinations of MAbs that effectively inhibit the growth of CCRF-CEM cells also inhibit the growth of HL-60 cells, a promyelocytic leukemic cell line, and of KG-1 cells, a human granulocytic leukemic cell line, by >90%. These combinations of MAbs also had smaller but readily detectable effects on the in vitro growth of K562 human erythroleukemic cells and M21 human melanoma cells. Both of these cell lines have previously been noted to be resistant to treatment with MAb 42/6 alone [Trowbridge, I. S., and Newman, R. A. Monoclonal antibodies to transferrin receptors. In: M. F. Greaves (ed.), Antibodies to Receptors: Probes for Receptor Structure and Function, pp. 235–262. London: Chapman & Hall (1985)]. The highest level of growth inhibition achieved by treatment of these two resistant cell lines with the combinations of two anti-Tf receptor MAbs was 40–50% in the 7 day assay. However, treatment of K562 cells with a combination of three MAbs, D65.30, A27.15 and B77.2, gave ~70% inhibition of growth.

EXAMPLE 4

Anti-tumor Effect of the MAb Combinations D65.30 with A27.15 and E2.3 with A27.15 In vivo. The effects of MAbs D65.30 and A27.15, both alone and in combination, on the growth of CCRF-CEM cells implanted at a subcutaneous (s.c.) site in nude mice were determined. In initial experiments, it was found that the combination of 3 mg each of D65.30 and A27.15 MAbs given intraperitoneally (i.p.) on days 0, 4 and 7 completely prevented the growth of tumors in all six mice challenged with a subcutaneous inoculum of $2\times10^7$ CCRF-CEM cells at a site on the back. Tumor growth was observed in the six control mice which received a subcutaneous inoculum of $2\times10^7$ CCRF-CEM cells at a site on the back. A combination of MAbs B3/25 and 42/6, administered intraperitoneally on days 0, 4, and 7, appeared only slightly less effective, preventing tumor growth in 4 out of 6 mice and delaying growth in the other two.

Figure 3:
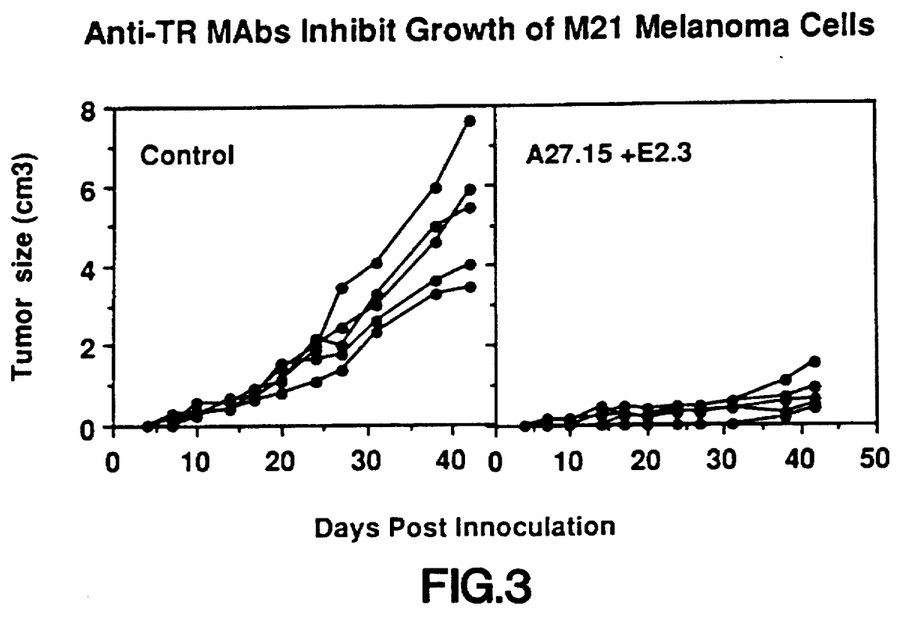
FIG. 3 shows graphs illustrating the effects upon mice that were inoculated subcutaneously with $2 \times 10^7$ M21 melanoma cells as described in Example 4. A dose of three mg each of the MAb combination E2.3 and A27.15 was administered to 5 mice intraperitoneally (ip) on days 0, 4, 7, 10, 14, and 17. Each line represents individual mice in each group.

In a similar experiment using a subcutaneous inoculum of $2\times10^7$ M21 melanoma cells, a combination of 3 mg each of the MAbs E2.3 and A27.15 was administered to 5 mice intraperitoneally on days 0, 4, 7, 10, 14, and 17. The results are shown in FIG. 3. The average growth in size of the M21 melanoma cells in the mice which received the E2.3/A27.15 MAb combination was less than 1 cm$^3$ measured over a 42-day period, whereas, the average growth observed in the 5 controls was approximately 5 cm$^3$ for the same period. Therefore, it can be stated that the E2.3/A27.15 MAb combination significantly inhibited the growth of M21 melanoma cells grown as a subcutaneous tumor.

It was thereafter investigated whether treatment with the combination of D65.30 and A27.15 MAbs would also inhibit the growth of established tumors. Mice were injected with $2\times10^7$ CCRF-CEM cells. Ten days later, the mice were divided into four groups, each containing 5 mice bearing a comparable range of tumor sizes. The four groups were then either (a) not treated, or injected (i.p.) on days 10, 14, 17, 21, 24 and 27 with (b) 3 mg of MAb D65.30 alone or (c) 3 mg of MAb A27.15 alone, or (d) 3 mg each of both MAbs.

Treatment with the combination of MAbs D65.30 and A27.15 had a striking effect on tumor growth. Marked inhibition of tumor growth was observed in all 5 of the mice treated with the combination of MAbs. In addition, in 3 of the 5 mice treated with the combination of MAbs D65.30 and A27.15, the tumors regressed. In contrast, in 3 of 5 mice treated with MAb D65.30 alone, tumors continued to grow at a similar rate to the untreated controls. In the remaining 2 mice treated with MAb D56.30 alone, the tumors exhibited little to no growth. Similarly, in 4 of 5 mice treated with MAb A27.15 alone, tumors continued to grow at a similar rate to the untreated controls. In the remaining mouse treated with MAb A27.15 alone, the tumor exhibited little to no growth.

The tumor growth rate in the untreated controls was from approximately 1–2 cm$^3$ at 10 days post-injection to approximately 20–25 cm$^3$ at 27 days post-injection. The tumor size was determined by two perpendicular measurements to tumor diameters, using calipers. Tumor size was then calculated according to the formula (Taetle et al., *Cancer Treat. Rep.*, 71:297–304, 1987):

$$\text{tumor size}=(\text{width, } cm)^2\times(\text{length, } cm)/2$$

A similar experiment was carried out to investigate whether treatment with the combination of E2.3 and A27.15 MAbs would also inhibit the growth of established tumors. Mice were injected with $2\times10^7$ CCRF-CEM cells. Ten days later, the mice were divided into five groups, each containing 5 mice bearing a comparable range of tumor sizes. The five groups were then either (a) not treated, or injected (i.p.) on days 10, 14, 17, 21, 24 and 27 with (b) 3 mg of MAb D65.30 alone or (c) 3 mg of MAb A27.15 alone, or (d) 3 mg each of both MAbs, or (e) 1.5 mg each of both MAbs.

Figure 4:
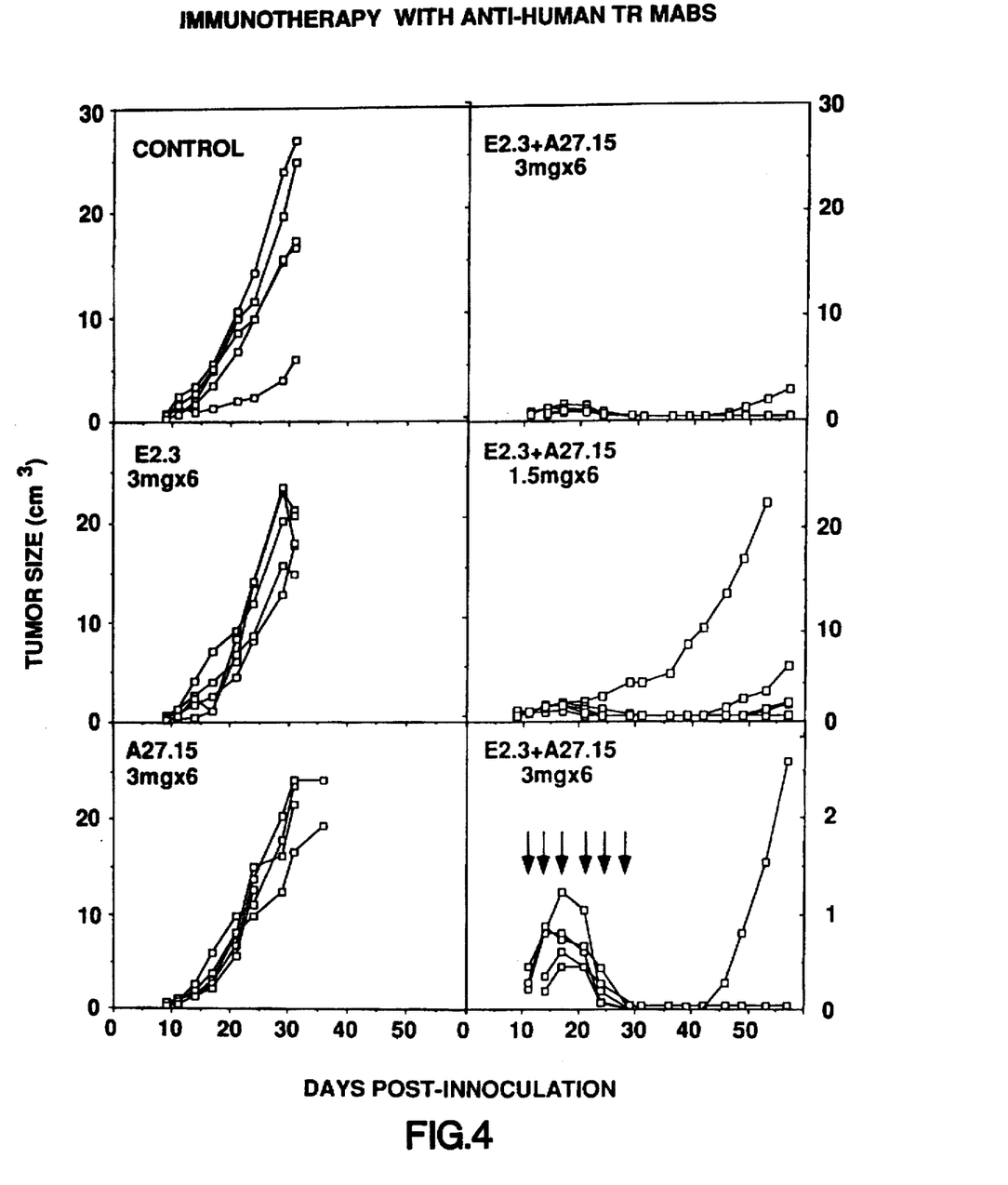
FIG. 4 shows graphs illustrating the effects upon mice that were injected with $2 \times 10^7$ CCRF-CEM cells and, 10 days later, were divided into five groups containing 5 mice bearing a comparable range of tumor sizes. The four groups were then either not treated, or injected ip on Days 10, 14, 17, 21, 24 and 27 with either 3 mg of MAb E2.3 alone or MAb A27.15 alone, or 3 mg each of both MAbs, or 1.5 mg of each of both MAbs, as described in Example 4. Each line represents individual mice in each group. The graph in the lower right hand corner is the same as that in the upper right hand corner but depicted on a 10-fold expanded scale.

The results of E2.3 and A27.15 MAb combination experiment are shown in FIG. 4. The data clearly shows that MAbs E2.3 and A27.15 alone are ineffective at inhibiting tumor growth. The tumor growth rate, from 0–20 cm$^3$ over approximately 40 days, for mice which received either MAbs E2.3 or A27.15 alone is approximately equivalent to that of the control mice.

In combination, however, there is regression of established tumors as shown in the upper right-hand panel of FIG. 4; the same data can be seen in greater detail in the lower right-hand panel of FIG. 4. The data for the mice which received 3 mg each of the E2.3/A27.15 MAb combination shows the tumors initially increasing in size similar to the control group. However, after the third dose of the MAb combination at day 17, all 5 tumors regressed completely with only 1 tumor recurring only slightly to approximately 2.5 cm$^3$ in size beginning at day 45. Therefore, the MAb combination E2.3 and A27.15 is capable of inhibiting subcutaneous CCRF-CEM tumor growth in mice.

In a related experiment various amounts of MAb A27.15 ranging from 0–3 mg in combination with 3 mg of MAb E2.3, and vice versa, were administered to groups of 4 mice on days 10, 14, 17, 21, 24, and 27 as described above. In the group which received 3 mg each of the MAb combination E2.3/A27.15, complete tumor regression occurred in 3 out of the 4 mice. In the remaining mouse of the group of 4, the growth rate of the tumor that developed was considerably slower than the tumor growth rate of the control group.

The anti-proliferative activity of combinations of anti-Tf receptor MAbs detected in vitro is capable of predicting anti-tumor activity in vivo, providing a convenient way of screening potential combinations of anti-human Tf MAbs for use in the invention. The combination of MAbs D65.30 and A27.15 had a striking effect on the growth of established subcutaneous CCRF-CEM tumors, leading in some cases to complete tumor regression. In contrast, neither MAb D65.30, nor A27.15 administered separately have marked inhibitory effects on tumor growth, clearly establishing that the in vivo anti-tumor effect of both MAbs together is the result of synergistic interactions. The same effect was also observed for the MAb combination E2.3 and A27.15.

EXAMPLE 5

Human Tf Binding and Internalization Studies. To determine the effects of anti-Tf receptor MAbs on cell surface Tf receptor expression and internalization, HL-60 cells were grown in 10 µg/ml of anti-Tf MAbs singly or in combination for 48 hours [Taetle, R., Castagnola, J., and Mendelsohn, J. in *Cancer Res.* 46:1759–1763 (1986).] Cells were then washed twice in serum-free RPMI 1640 medium and incubated with saturating amounts of $^{125}$I-labelled dimeric human Tf at 4° C. for 60 min. The cells were washed three times in serum-free medium and counted in a gamma counter. Non-specific binding was determined in the presence of a 100-fold excess of unlabelled human Tf, and these values were subtracted from total cell binding.

To determine the effect of anti-Tf receptor MAbs on the internalization of human Tf, cells were grown in the presence or absence of MAbs for 48 hours as described above. The cells were then washed, incubated in $^{125}$I-labelled human Tf at 4 µg/ml for 30 min. at 4° C., then, at 37° C. for 30–45 min. to allow the steady-state intracellular and cell surface distribution of Tf receptors to be established. Cells were then washed three times at 4° C. with 1 ml saline and then incubated for 5 min. at 4° C. with 0.5M NaCl –0.2M acetic acid to remove surface-bound Tf, as described by Taetle, R., Castagnola, J., and Mendelsohn, J., supra. For HL-60 cells, this procedure was shown to remove greater than 95% of $^{125}$I-labelled Tf bound at 4° C. The remaining internalized acid-resistant radioactivity in the cell pellet was then determined in a gamma counter.

Inhibition studies of Human Tf Binding. The ability of anti-Tf receptor MAbs to inhibit $^{125}$I-labelled Tf binding to the Tf receptor were performed as previously described by Jing, S., Spencer, T., Miller, K., Hopkins, C., and Trowbridge, I. S. [*J. Cell Biol.* 110:283–294 (1990)], except that chicken embryo fibroblasts expressing "tailless" mutant human Tf receptors were used instead of CCRF-CEM cells [Trowbridge, I. S. and Lopez, F. in *Proc. Natl. Acad. Sci. USA* 79:1175–1179 (1982)]. Cells (1×10$^5$ per well) were plated in Costar 24-well tissue culture plates and incubated overnight. Cells were washed three times with Dulbecco's modified Eagle's medium (DMEM) at 4° C. and then triplicate wells incubated for 1 h at 4° C. with 150 ml of DMEM containing various concentrations of anti-Tf receptor MAbs. Cells were washed three times with DMEM and then incubated for 1 h at 4° C. with 150 µl of $^{125}$I-labelled human Tf (4 µg/ml; space ~2 µCi per mg) in DMEM containing 0.5% (w/v) bovine serum albumin. Cells were washed three times, removed from the wells with 1M NaOH and counted in a gamma counter.

All the MAbs listed in Table 1 were tested for their ability to block human Tf binding to the Tf receptor. Under conditions in which 42/6 inhibited Tf binding by >90%, none of the other MAbs tested inhibited Tf binding. Further, Tf binding was not inhibited by combinations of MAbs with high anti-proliferative activity.

The effects of prolonged exposure of cells to anti-Tf receptor MAbs either singly or in combination on Tf receptor expression are presented in Table 2.

Treatment for 48 hours with either single MAbs or pairs of MAbs, with the exception of A27.15 alone, caused a substantial reduction in surface Tf receptor expression determined by Tf binding at 4° C. In a separate set of experiments, a similar reduction in the total number of Tf receptors determined by Tf binding at 37° C. was also observed after 48 hours of MAb treatment.

In addition to reducing the expression of Tf receptors, MAb treatment also perturbed their steady-state intracellular distribution. Testing showed that a much smaller fraction of the remaining Tf receptors of cells treated with 42/6 alone, as compared to the combinations B3/25 and 42/6, or D65.30 and A27.15, were intracellular compared to that for the untreated control cells or cells treated with single IgG anti-Tf receptor MAbs alone.

EXAMPLE 6

Combinations of Anti-Tf Receptor MAbs are Cytotoxic. To evaluate whether growth inhibition caused by the inventive method is because the combination of anti-Tf receptor MAbs are cytostatic or cytotoxic, a quantitative estimate of the cytotoxic effects of combinations of anti-Tf receptor MAbs on HL-60 colony formation was determined. Two combinations of anti-Tf receptor MAbs were used: B3/25+ 42/6 and D65.30+A27.15, which combinations were among the most effective at inhibiting the growth of leukemic cell lines and represented two different kinds of effective MAb combinations. One is a combination of two MAbs, an IgG and IgA; the other is a combination of two IgG$_1$MAbs, each with anti-proliferative activity alone.

HL-60 cells were cultured in the presence of 10 µg/ml of each MAb, either alone or in combination, washed, and then equal numbers of cells were replated in the colony-forming assay in the absence of MAbs.

Each of the MAb combinations was observed to have a profound effect upon colony formation. After two days, colony formation by cells treated with either the combination of MAbs 42/6 and B3/25 or of MAbs D65.30 and A27.15, was inhibited by >90%. After five days, the MAb combinations inhibited colony formation by >95%, clearly demonstrating that prolonged exposure to the MAbs was cytotoxic.

TABLE 2

Tf binding and internalization after culture with anti-transferrin receptor MAbs.[a]

|  | Control | 42/6 | B3/25 | 42/6 + B3/25 | D65.30 | A27.15 | D65.30 + A27.15 |
| --- | --- | --- | --- | --- | --- | --- | --- |
| Tf Binding at 4° C. | 40906 ± 1682[b] | 15 ± 7[c] | 31 ± 2 | 16 ± 7 | 16 ± 3 | 80 ± 14 | 26 ± 4 |
| Total Tf Binding at 37° C. | 36173 ± 7460 | 39 ± 17 | 52 | 29 ± 9 | 19 ± 7 | 92 ± 14 | 34 ± 8 |
| Total % Tf Internalized | 53 ± 3[d] | 21 ± 7 | 58 ± 4 | 15 ± 12 | 80 ± 5 | 43 ± 6 | 27 ± 6 |

[a]HL60 leukemia cells were grown with 10 µg/ml of anti-Tf receptor MAbs alone or in combination for 48 hours. Surface Tf binding sites were assessed by Tf binding at 4° C. Tf internalization was assessed by saturating surface Tf binding sites at 4° C. and warming cells to 37° C. for 30–45 minutes. In separate experiments, 37° C. (surface and internalized) and internalized (acid stable) Tf were also determined. Control cells at 37° C. internalized 53 ± 3% of Total Tf. Results are the means of duplicate or means ± SE of three experiments.
[b]$^{125}$I-labelled Tf binding expressed as cpm per 10$^6$ cells.
[c]Percent of binding by untreated cells.
[d]Percent of total Tf bound at 37° C. resistant to acid wash.

What is claimed is:

1. A therapeutic composition for inhibiting proliferation of transferrin-receptor-positive tumor cells expressing the transferrin receptor on their surfaces, said composition comprising a combination of a first and a second monoclonal antibody and a pharmaceutically acceptable carrier, wherein each of said antibodies is an anti-human-transferrin-receptor monoclonal antibody which binds to an epitope of the external domain of the human transferrin receptor glycoprotein and which first and second monoclonal antibodies simultaneously bind the transferrin receptor, wherein in vitro screening of the CCRF-CEM leukemic cell line with said first and second monoclonal antibodies individually and with said combination of said first and second monoclonal antibodies shows that said combination inhibits cell proliferation to a greater extent than either of said antibodies individually and also inhibits cell proliferation by at least about 80%, and wherein said combination of antibodies inhibits in vivo proliferation of cells expressing the transferrin receptor on their surfaces selected from the group consisting of human hematopoietic tumor cells and human melanoma cells by binding the transferrin receptor and thereby blocking transferrin receptor function.

2. A composition according to claim 1 wherein said first antibody individually does not exhibit significant activity to inhibit tumor cell proliferation when subjected to in vitro screening of the CCRF-CEM leukemic cell line, inhibiting growth of said CCRF-CEM cells by less than about 50%.

3. A composition according to claim 2 wherein said first antibody does not block the binding of transferrin to said receptor glycoprotein.

4. A composition according to claim 2 wherein said second antibody individually has a significant inhibiting effect upon tumor cell proliferation when subjected to in vitro screening of the CCRF-CEM leukemic cell line, inhibiting growth of said CCRF-CEM cells by at least about 60%.

5. A composition according to claim 4 wherein said second antibody individually blocks the binding of transferrin to said receptor glycoprotein.

6. A composition according to claim 1 wherein both said first and second antibodies are IgG antibodies.

7. A composition according to claim 1 wherein at least one of said antibodies is an $IgG_1$ antibody.

8. A composition for inhibiting the proliferation of transferrin-receptor-positive tumor cells expressing the human transferrin receptor on their outer surfaces, which composition comprises first and second monoclonal antibodies in a pharmaceutically acceptable carrier, each of said monoclonal antibodies is an anti-human-transferrin-receptor monoclonal antibody which specifically binds to an epitope of the external domain of the human transferrin receptor glycoprotein, said first monoclonal antibody being one obtained from a cell line selected from the group of cell lines consisting of that designated B3/25 and assigned ATCC Accession No. CRL-8034, that designated A27.15 and assigned ATCC Accession No. HB-10395, and an antibody-producing reclone of either of said aforementioned cell lines, which reclone produces antibodies that bind to epitopes of the external domain of said human transferrin receptor glycoprotein, said second monoclonal antibody being one obtained from a cell line selected from the group of cell lines consisting of that designated 42/6 and assigned ATCC Accession No. HB-8094, that designated D65.30 and assigned ATCC Accession No. HB-10394, that designated E2.3 and assigned ATCC Accession No. CRL 20746, and an antibody-producing reclone of any one of said aforementioned cell lines, which reclone produces antibodies that bind to epitopes of the external domain of said human transferrin receptor glycoprotein, wherein said first and second monoclonal antibodies simultaneously bind the human transferrin receptor and the composition inhibits proliferation of said cells to a greater extent than either of the antibodies separately by binding the transferrin receptor and thereby blocking transferrin receptor function.

9. A composition according to claim 8 wherein said first monoclonal antibody is one obtained from the cell line designated B3/25 and assigned ATCC Accession No. CRL-8034, or an antibody-producing reclone thereof which reclone produces antibodies that bind to the external domain of said human transferrin receptor glycoprotein and wherein said second monoclonal antibody is one obtained from the cell line designated 42/6 and assigned ATCC Accession No. HB-8094, or an antibody-producing reclone thereof which reclone produces antibodies that bind to the external domain of said human transferrin receptor glycoprotein.

10. A method of inhibiting proliferation of transferrin-receptor-positive cells expressing the transferrin receptor on their surfaces in a human, which method comprises administering to said human an effective dose of a combination containing a first and a second monoclonal antibody, which dose is effective to halt proliferation of said cells, wherein each of said antibodies is an anti-human-transferrin-receptor monoclonal antibody which binds to an epitope of the external domain of the human transferrin receptor glycoprotein and which first and second monoclonal antibodies simultaneously bind the transferrin receptor, said first and second antibodies being such that a comparison of in vitro screening of the CCRF-CEM leukemic cell line with said first and second monoclonal antibodies individually and in vitro screening thereof with said combination of said first and second monoclonal antibodies shows that said combination inhibits cell proliferation to a greater extent than either of said antibodies individually and also inhibits cell proliferation by at least about 80%, and wherein said dose of said combination of antibodies inhibits in vivo cell proliferation of cells expressing the transferrin receptor on their surfaces selected from the group consisting of human hematopoietic tumor cells and human melanoma cells by binding the transferrin receptor and thereby blocking transferrin receptor function.

11. A method according to claim 10 wherein said first antibody individually has substantially no inhibiting effect upon tumor cell proliferation when subjected to in vitro screening of the CCRF-CEM leukemic cell line.

12. A method according to claim 10 wherein said first antibody does not block the binding of transferrin to said receptor glycoprotein.

13. A method according to claim 11 wherein said second antibody individually has a significant inhibiting effect upon tumor cell proliferation when subjected to in vitro screening of the CCRF-CEM leukemic cell line, inhibiting growth of said CCRF-CEM cells by at least about 60%.

14. A method according to claim 10 wherein both said first and second antibodies are IgG antibodies.

15. A method according to claim 10 wherein said combination of antibodies is administered intravenously or intraperitoneally to the recipient being treated at a daily dosage level of said combination of antibodies of at least about 0.1 mg per kilogram of body weight.

16. A method according to claim 10 wherein said combination of antibodies is administered intravenously or intraperitoneally to the recipient to be treated at a daily dosage level sufficient to bring the concentration of said combination of antibodies in the serum of the recipient to at least about 1 µg/ml.

17. A method according to claim 10 wherein said combination of antibodies is administered intravenously or intraperitoneally to the recipient to be treated at a daily dosage level sufficient to bring the concentration of said combination of antibodies in the serum of the recipient to at least about 10 µg/ml.

18. A method according to claim 10 wherein said method is employed for the treatment to inhibit leukemia cell proliferation or erythroleukemic tumor cell proliferation.

19. A method according to claim 10 wherein said first monoclonal antibody is one obtained from a cell line selected from the group of cell lines consisting of that designated B3/25 and assigned ATCC Accession No. CRL-8034, that designated A27.15 and assigned ATCC Accession No. HB-10395, and an antibody-producing reclone of either of said aforementioned cell lines which reclone produces antibodies that bind to the external domain of said human transferrin receptor glycoprotein.

20. A method according to claim 10 wherein at least one of said antibodies is an IgG$_1$ antibody.

21. A method according to claim 19 wherein said second monoclonal antibody is one obtained from a cell line selected from the group of cell lines consisting of that designated 42/6 and assigned ATCC Accession No. HB-8094, that designated D65.30 and assigned ATCC Accession No. HB-10394, that designated E2.3 and assigned ATCC Accession No. CRL 10746, and an antibody-producing reclone of any one of said aforementioned cell lines which reclone produces antibodies that bind to the external domain of said human transferrin receptor glycoprotein.

22. A method of inhibiting proliferation of tumor cells expressing the transferrin receptor on their surfaces in a human, which method comprises administering to said human an effective dose of a combination containing a first monoclonal antibody and a second monoclonal antibody which dose is effective to halt proliferation of said cells, wherein each of said antibodies binds to an epitope of the external domain of the human transferrin receptor glycoprotein, said first monoclonal antibody being one obtained from the cell line designated A27.15 and assigned ATCC Accession No. HB-10395 or an antibody-producing reclone thereof which reclone produces antibodies that bind to epitopes of the external domain of said human transferrin receptor glycoprotein, and said second monoclonal antibody being one obtained from the cell line designated E2.3 and assigned ATCC Accession No. CRL 10746 or an antibody-producing reclone thereof which reclone produces antibodies that bind to epitopes of the external domain of said human transferrin receptor glycoprotein, wherein said first and second monoclonal antibodies simultaneously bind the human transferrin receptor and wherein said dose of said combination of antibodies inhibits in vivo cell proliferation of cells expressing the transferrin receptor on their surfaces selected from the group consisting of human hematopoietic tumor cells and human melanoma cells by binding the transferrin receptor and thereby blocking transferrin receptor function.

23. A composition according to claim 8 wherein said first monoclonal antibody is one obtained from the cell line designated A27.15 and assigned ATCC Accession No. HB-10395 or an antibody-producing reclone of said cell line, which reclone produces antibodies that bind to the exterior domain of said human transferrin receptor glycoprotein, and wherein said second monoclonal antibody is one obtained from the cell line designated D65.30 and assigned ATCC Accession No. HB-10394, or an antibody-producing reclone of said cell line, which reclone produces antibodies that bind to the external domain of said human transferrin receptor glycoprotein.

24. A composition according to claim 8 wherein said first monoclonal antibody is one obtained from the cell line designated A27.15 and assigned ATCC Accession No. HB-10395 or an antibody-producing reclone of said cell line, which reclone produces antibodies that bind to the exterior domain of said human transferrin receptor glycoprotein, and wherein said second monoclonal antibody is one obtained from the cell line designated E2.3 and assigned ATCC Accession No. CRL-10746, or an antibody-producing reclone of said cell line, which reclone produces antibodies that bind to the external domain of said human transferrin receptor glycoprotein.

* * * * *